US00RE45922E

(19) United States
(12) Reissued Patent
Marcovecchio et al.

(10) Patent Number: US RE45,922 E
(45) Date of Reissued Patent: *Mar. 15, 2016

(54) PROCESSING PULSE SIGNAL IN CONJUNCTION WITH ACCELEROMETER SIGNAL IN CARDIAC RESUSCITATION

(71) Applicant: ZOLL Medical Corporation, Chelmsford, MA (US)

(72) Inventors: Alan F. Marcovecchio, San Clemente, CA (US); Frederick Geheb, Sr., Danvers, MA (US); Donald R. Boucher, Andover, MA (US)

(73) Assignee: ZOLL Medical Corporation, Chelmsford, MA (US)

( * ) Notice: This patent is subject to a terminal disclaimer.

(21) Appl. No.: 13/872,037

(22) Filed: Apr. 26, 2013

Related U.S. Patent Documents

Reissue of:
(64) Patent No.: 7,488,293
Issued: Feb. 10, 2009
Appl. No.: 11/228,857
Filed: Sep. 15, 2005

U.S. Applications:
(63) Continuation of application No. 13/025,124, filed on Feb. 10, 2011, now Pat. No. Re. 44,187, which is an application for the reissue of Pat. No. 7,488,293, which is a (Continued)

(51) Int. Cl.

| | |
|---|---|
| ***A61H 31/00*** | (2006.01) |
| ***A61B 5/0205*** | (2006.01) |
| ***A61B 5/021*** | (2006.01) |
| ***A61B 5/11*** | (2006.01) |
| *A61B 5/024* | (2006.01) |

(52) U.S. Cl.
CPC ..... *A61H 31/00* (2013.01); *A61B 5/021* (2013.01); *A61B 5/0205* (2013.01); *A61B 5/11* (2013.01); *A61B 5/024* (2013.01); *A61H 31/005* (2013.01)

(58) Field of Classification Search
None
See application file for complete search history.

(56) References Cited

U.S. PATENT DOCUMENTS

| | | | |
|---|---|---|---|
| 3,903,873 | A | 9/1975 | Royal et al. |
| 4,052,979 | A | 10/1977 | Scherr et al. |

(Continued)

FOREIGN PATENT DOCUMENTS

| | | |
|---|---|---|
| JP | 98/26716 | 6/1988 |
| JP | 4015038 | 1/1992 |

(Continued)

OTHER PUBLICATIONS

Kassal et al., "Polymer-Based Adherent Differential-Output Sensor for Cardiac Auscultation," Medical Electronics, vol. 25, No. 4, Issue 148, pp. 54-63 (Sep. 1994).

(Continued)

*Primary Examiner* — Kennedy Schaetzle
(74) *Attorney, Agent, or Firm* — Fish & Richardson P.C.

(57) ABSTRACT

A cardiac resuscitation device that includes a pulse sensor configured to detect pulse information characterizing the cardiac pulse in the patient, an accelerometer configured to detect chest movements of the patient during chest compressions, and memory and processing circuits configured to process the outputs of the pulse sensor and accelerometer to monitor the effect that chest compressions have on the patient's pulse.

4 Claims, 10 Drawing Sheets

Related U.S. Application Data continuation of application No. 10/441,933, filed on May 20, 2003, now abandoned, which is a continuation-in-part of application No. 10/421,652, filed on Apr. 23, 2003, now abandoned.

(56) References Cited

U.S. PATENT DOCUMENTS

| | | | | |
|---|---|---|---|---|
| 4,299,233 | A | | 11/1981 | Lemelson |
| 4,331,154 | A | | 5/1982 | Broadwater |
| 4,443,730 | A | | 4/1984 | Kitamura et al. |
| 4,722,347 | A | | 2/1988 | Abrams et al. |
| 4,911,167 | A | | 3/1990 | Corenman et al. |
| 4,987,783 | A | | 1/1991 | D'Antonio et al. |
| 5,086,776 | A | | 2/1992 | Fowler, Jr. et al. |
| 5,409,009 | A | | 4/1995 | Olson |
| 5,431,685 | A | | 7/1995 | Alt |
| 5,496,257 | A | * | 3/1996 | Kelly ..... 601/41 |
| 5,588,425 | A | | 12/1996 | Sackner et al. |
| 5,595,188 | A | | 1/1997 | Kassal |
| 5,645,571 | A | | 7/1997 | Olson et al. |
| 5,795,300 | A | | 8/1998 | Bryars |
| 5,807,267 | A | | 9/1998 | Bryars et al. |
| 5,807,268 | A | | 9/1998 | Reeves |
| 5,827,198 | A | | 10/1998 | Kassal |
| 5,885,222 | A | | 3/1999 | Kassal et al. |
| 5,913,829 | A | | 6/1999 | Reeves et al. |
| 5,991,661 | A | | 11/1999 | Park et al. |
| 6,298,267 | B1 | | 10/2001 | Rosborough et al. |
| 6,304,773 | B1 | | 10/2001 | Taylor et al. |
| 6,356,785 | B1 | | 3/2002 | Snyder et al. |
| 6,440,082 | B1 | | 8/2002 | Joo et al. |
| 6,487,442 | B1 | | 11/2002 | Wood |
| 6,567,697 | B1 | | 5/2003 | Kroll et al. |
| 6,575,914 | B2 | | 6/2003 | Rock et al. |
| RE44,187 | E | * | 4/2013 | Marcovecchio et al. ..... 600/504 |
| 2001/0047140 | A1 | | 11/2001 | Freeman |
| 2002/0165585 | A1 | | 11/2002 | Dupelle |
| 2002/0173725 | A1 | | 11/2002 | Rock et al. |
| 2003/0060723 | A1 | | 3/2003 | Joo et al. |
| 2004/0039420 | A1 | | 2/2004 | Jayne et al. |

FOREIGN PATENT DOCUMENTS

| | | |
|---|---|---|
| JP | 4028344 | 1/1992 |
| JP | 4028345 | 1/1992 |
| JP | 5261071 | 10/1993 |
| JP | 7265272 | 10/1995 |
| WO | 95/06525 | 3/1995 |
| WO | 98/26716 | 6/1998 |
| WO | 01/22885 | 4/2001 |

OTHER PUBLICATIONS

Webster, John G., Medical Instrumentation, Application and Design, 3rd ed., New York, NY, John J. Wiley & Sons, Inc. 1998.

* cited by examiner

Reusable Finger Sensor

Disposable Finger Sensor

| ECG Analysis | Optical Pulse Analysis | Resultant Therapy (ECG Only) | Resultant Therapy (ECG & Pulse) |
|---|---|---|---|
| Shock Advised | Pulse Detected | Shock Advised | No Shock Advised |
| No Shock Advised | Pulse Detected | No Shock Advised | No Shock Advised |
| Shock Advised | No Pulse Detected | Shock Advised | Shock Advised |
| No Shock Advised | No Pulse Detected | No Shock Advised | CPR Advised |

FIG. 9

Reflectance Sensor

Transmittance Sensor

PROCESSING PULSE SIGNAL IN CONJUNCTION WITH ACCELEROMETER SIGNAL IN CARDIAC RESUSCITATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a *continuation reissue application of U.S. Pat. No. 7,488,293, and is with U.S. patent application Ser. No. 13/025,124, filed on Feb. 10, 2011, now issued U.S. Pat. No. RE44,187, another reissue application of the '293 patent; the '293 patent issued on U.S. patent application Ser. No. 11/228,857, filed on Sep. 15, 2005, which application is a* continuation of U.S. patent application Ser. No. 10/441,933, filed on May 20, 2003, now abandoned, which is a continuation in part application of U.S. patent application Ser. No. 10/421,652, entitled "Optical Pulse Sensor for External Defibrillator," filed on Apr. 23, 2003, now abandoned.

TECHNICAL FIELD

This invention relates to pulse sensors and methods of using pulse sensors in conjunction with external defibrillators.

BACKGROUND

The pulse is a very important parameter that is used to aid users of automated external defibrillators in determining whether or not to administer a defibrillation shock to and/or to perform cardiopulmonary resuscitation (CPR) on a victim who appears to be in cardiac arrest. Such a victim may actually be in need of cardiac resuscitation (including defibrillation and/or CPR), or may be suffering from a condition for which such treatment would be unsuitable, e.g., a stroke, seizure, diabetic coma, or heat exhaustion. It is very important to the safety of the victim that the presence or absence of a pulse be determined quickly and accurately. However, it is often difficult for trained medical personnel to take a victim's pulse accurately in the field during a crisis situation, and may be impossible for a minimally trained or untrained lay rescuer to do so. In many cases, it will take the person assisting the victim a considerable time (on the order of one minute or more) to find the victim's pulse. If a pulse is not found, the caregiver is left unsure as to whether the victim does not have a pulse, or whether the caregiver simply cannot find the victim's pulse.

Another parameter that is used in determining whether to administer a defibrillation shock is an ECG analysis of the victim's heart rhythm that is provided by the automated external defibrillator. Based on the ECG analysis, many automated defibrillators will provide the user with a message indicating whether a shock should be administered (i.e., whether or not ventricular fibrillation is present).

Generally, the ECG analysis systems in most commercially available automated external defibrillators display only two options to the user: "Shock Advised" or "No Shock Advised." When "Shock Advised" is output, this means that the patient is in ventricular fibrillation or wide complex ventricular tachycardia above 150 BPM, conditions which are effectively treated by defibrillation. When "No Shock Advised" is output, this means that the patient's heart rhythm is not treatable by defibrillation therapy.

If the message indicates that a shock is not appropriate, this does not necessarily mean that the victim is not in danger. There are two ECG rhythms, generally referred to as asystole and pulseless electrical activity, which should not be treated with defibrillation (and thus will trigger a message not to shock) but nonetheless are extremely serious in that they suggest that the patient's heart rhythm is unaccompanied by sufficient cardiac output (i.e., the patient is close to death). These conditions are treated by administering cardiopulmonary resuscitation (CPR), in an effort to provide blood flow to the heart and vital organs in the hope that with improved blood flow and oxygenation, the heart muscle will recover from its near death state and possibly begin to fibrillate again, thus making defibrillation treatment a viable option.

Thus, when a "No Shock Advised" analysis is output, the caregiver does not know whether this result is caused by a normal heart rhythm, an abnormal but perfusing heart rhythm (i.e., the patient was never in cardiac arrest or the last shock treatment returned the patient's heart rhythm to normal), or a grossly abnormal (non-perfusing) ECG rhythm requiring CPR treatment. Because of this uncertainty, the normal medical protocol when "No Shock Advised" is output is to check the patient for a pulse and if no pulse is detected to start CPR. If a pulse is detected, then the patient's heart is effectively pumping blood and neither CPR nor defibrillation is warranted. If the victim does not have a pulse, CPR should be started immediately; if a pulse is present, then CPR should not be administered. Because CPR, even if properly administered, can result in broken ribs or other injury to the victim, it is undesirable to administer CPR if it is not actually necessary. Thus, it is again vitally important that an accurate determination of the presence or absence of a pulse be made by the caregiver.

A similar situation of uncertainty occurs after the third defibrillation shock is delivered in the three-shock protocol recommended by the American Heart Association. In this case, if the patient's fibrillation has not been "cured" after delivery of three shocks, the caregiver is instructed to perform CPR on the patient. Because automated external defibrillators generally do not perform an ECG analysis immediately after the third shock, the caregiver does not know whether the third shock provided effective treatment. Therefore, the caregiver must determine whether the patient has a pulse in order to determine whether CPR is needed or whether the patient is out of danger.

A wide variety of sensors have been employed for pulse detection.

Optical sensors have been used in pulse detection. For example, pulse detectors of the type used for measuring heart rate during exercise typically rely on reflectance or transmission of an infrared light beam. Blood pulsing in the user's capillaries produces a corresponding variation in the absorption of light by capillaries, and that variation produces a pulsation in the output of an optical sensor.

Optical sensors are also widely used in pulse oximetry, in which a measurement is made of the percentage of hemoglobin saturated with oxygen. An optical plethysmographic probe attached to the patient's finger or ear lobe generates light at two wavelengths (e.g., 650 nm and 805 nm). The light is partially absorbed by hemoglobin, by amounts that differ depending on whether or not the hemoglobin is saturated with oxygen. By calculating absorption at the two wavelengths, a pulse oximetry device can compute the proportion of hemoglobin that is saturated (oxygenated).

Acoustic sensors have also been applied to pulse detection. Typically, the acoustic sensor is configured to detect sounds characteristic of a beating heart (e.g., the action of a heart valve). E.g., Joo U.S. Pat. No. 6,440,082. Some acoustic sensors used for pulse detection are based on piezoelectric devices.

Another use of a piezoelectric devices in pulse detection is proposed in U.S. patent application Ser. No. 9/846,673, filed on May 1, 2001. The piezoelectric device detects motion of the surface of the body resulting from the pulse (e.g., motion resulting from blood flowing in a blood vessel beneath the sensor).

SUMMARY

In a first aspect, the invention features a cardiac resuscitation device, comprising a pulse sensor configured to detect pulse information characterizing the cardiac pulse in the patient, wherein the pulse sensor has a pulse sensor output signal as its output, an accelerometer configured to detect chest movements of the patient during chest compressions, wherein the accelerometer has an accelerometer output signal as its output, and memory and processing circuits configured to process the pulse sensor output signal and accelerometer output signal to monitor the effect that chest compressions have on the patient's pulse.

In a second aspect, the memory and processing circuits may be configured to process the pulse sensor output signal in conjunction with the accelerometer output signal to provide information to the user of the device to improve delivery of CPR to the patient.

In a third aspect, the memory and processing circuits may be configured to process the pulse sensor output signal in conjunction with the accelerometer output signal to determine if chest compressions actually result in the movement of blood thus resulting in a pulse.

In preferred implementations, one or more of the following features may be incorporated. The device may comprise a defibrillator for delivering a defibrillation waveform to the patient and chest electrodes for detecting at least one ECG signal on the patient and for delivering a defibrillation waveform to the patient. The memory and processing circuits may be further configured to analyze the pulse sensor output signal in conjunction with the ECG signal to determine whether the patient has a pulse. The pulse rate of the pulse signal may be compared to the pulse rate of the ECG signal. The memory and processing circuits may be configured to process the accelerometer output signal to determine the rate and depth of delivered chest compressions. The memory and processing circuits may be configured to process the pulse sensor output signal to determine the magnitude and frequency of the patient's pulse. A decision whether to deliver a defibrillation waveform to the patient may be based in part on whether processing of the ECG and pulse sensor output signals determines that the patient has a pulse. The defibrillator may comprise an automatic external defibrillator (AED). The invention may further comprise the capability to provide the user with prompts for performing CPR, and wherein the prompts may be dependent at least in part on whether the processing of the pulse signal determines that the patient has a pulse. A determination of whether the patient has a pulse may be undertaken after delivery of the defibrillation waveform, and the user may be informed of the outcome of the determination. The memory and processor circuits may be further configured to make a determination whether to administer CPR to the patient and the determination may be based at least in part on whether it is determined that the patient has a pulse. The memory and processing circuits may be further configured to use the pulse sensor output signal to determine the efficacy of CPR treatment of the patient.

In a further aspect, the inventors have found that an external defibrillator can be configured to determine whether a patient has a pulse by analyzing the output of a pulse sensor in conjunction with the patient's ECG signal to determine whether a pulse is present. In general the invention features applying electrodes to the chest of the patient, detecting at least one ECG signal from electrodes, applying a pulse sensor (of varying kinds) to the patient, detecting a pulse signal from the pulse sensor, and analyzing the pulse signal in conjunction with the ECG signal to determine whether the patient has a pulse.

Preferred implementations of this aspect of the invention may incorporate one or more of the following: The pulse rate of the pulse signal may be compared to the pulse rate of the ECG signal. The pulse signal may be processed to isolate the pulsatile component of the signal. The pulse signal may be examined for a peak during a window initiated at the occurrence of an R-wave in the ECG signal. A comparison may be made of the energy in discrete frequency bands of the pulse and the ECG signals. A peak frequency corresponding to the peak of one of the pulse and ECG signals may be determined, and the other of the pulse and ECG signals may be examined for a peak within a frequency band surrounding the peak frequency. A frequency domain transformation of the pulse signal may be processed. The frequency domain transformations of the pulse and ECG signal may be processed. A decision whether to deliver a defibrillation waveform to the patient may be based in part on whether processing of the ECG and pulse signals determines that the patient has a pulse. The defibrillator may be an automatic external defibrillator (AED). The implementation may include the capability to provide the user with prompts for performing CPR, wherein the prompts are dependent at least in part on whether the processing of the pulse signal determines that the patient has a pulse. A determination of whether the patient has a pulse may be undertaken after delivery of the defibrillation waveform, and the user may be informed of the outcome of the determination. The pulse sensor (e.g., an optical plethysmographic sensor) may be mechanically connected to at least one of the defibrillation electrodes. There may be two defibrillation electrodes, each supported on a substrate, and the pulse sensor may be supported on the same substrate. The wires connected to the pulse sensor may be bundled with wires connected to the defibrillation electrodes to form a combined bundle of wires extending from the defibrillator to the electrodes and sensor. The pulse sensor may be mechanically separate from the defibrillation electrodes. In the case of an optical pulse sensor, the sensor may be configured to be attached to the forehead of the patient to the ear lobe, to the nasal septum, to the nasal bridge, or to the finger. In the case of an optical pulse sensor, the sensor may be configured so that its output may also be used for pulse oximetry, or it may be configured so that its output is not useful for pulse oximetry. Determining whether the patient has a pulse may include determining whether the pulse, if present, is correlated with the R-wave of the patient's heart rhythm. A determination whether to administer CPR to the patient may be based on whether it is determined that the patient has a pulse. The pulse sensor may be to determine the efficacy of CPR treatment of the patient. Analyzing the pulse signal in conjunction with the ECG signal may comprise analyzing whether there is a correlation between the two signals indicative of the presence of a pulse.

A wide variety of pulse sensors may be used. The pulse sensor may include a non-optical sensor. The pulse sensor may be an acoustic (heart sounds) sensor. The pulse sensor may include an ultrasonic blood flow sensor. The pulse sensor may include a pressure sensor on a limb-compressing pneumatic cuff. The pulse sensor may include at least one mechanical or ultrasonic sensor (e.g., a piezoelectric sensor) configured to detect arterial wall motion caused by blood flow in an artery. The pulse sensor may include one or more sensors for measuring body impedance variation from blood flow.

Implementations of the invention have many and various advantages. They can make it possible to perform a quick and accurate determination of the appropriate treatment (defibrillation, CPR, or no cardiac-related treatment) for a patient who appears to be suffering from cardiac arrest. They can provide an accurate determination of the presence or absence of a pulse in a patient, even under adverse conditions, thus significantly reducing the risk that an inappropriate and even dangerous treatment will be given erroneously. The accurate pulse determination thus provided relieves the uncertainty experienced by caregivers in the circumstances discussed above, and thus increases the likelihood of the patient receiving prompt, safe and effective treatment. For example, a pulse sensor can be used to determine whether CPR is necessary, in the event that an automated defibrillator indicates that it is not appropriate to shock a patient who appears to be suffering from cardiac arrest.

In some implementations, in which the pulse sensor is an optical sensor, the invention provides an optical sensor without the complexity of pulse oximetry, in which two optical measurements, one at each of two wavelengths, are made, and complex signal processing is performed to estimate blood oxygen saturation from the two measurements.

Other features and advantages of the invention will be apparent from the drawings, detailed description, and claims.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 9 is a table summarizing a decision algorithm used in one implementation of the invention.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
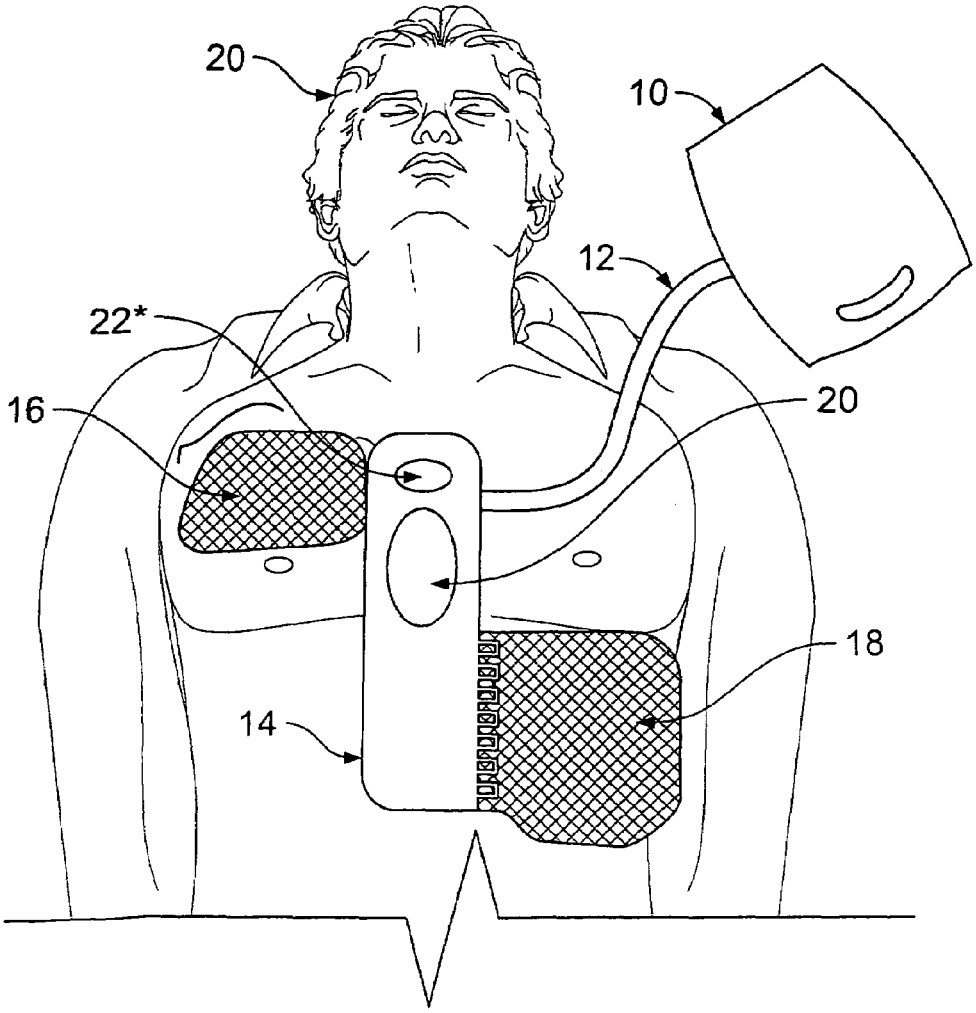
FIG. 1 is a diagrammatic, perspective view of an electrode pad with built-in pulse sensor applied to the chest of patient.
Figure 2A:
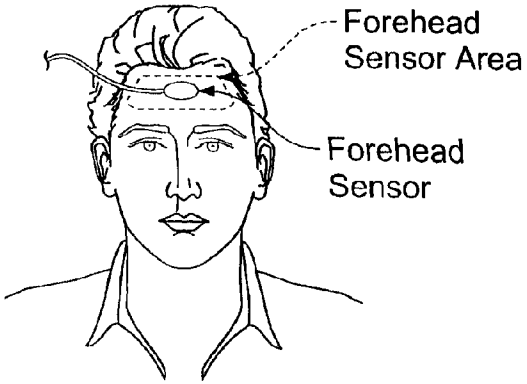
FIGS. 2A-2F are diagrammatic views of other possible pulse sensors applied to the patient.
Figure 2B:
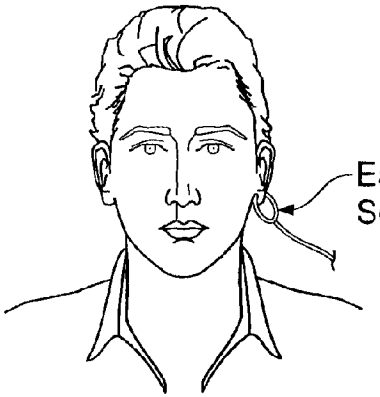
Figure 2C:
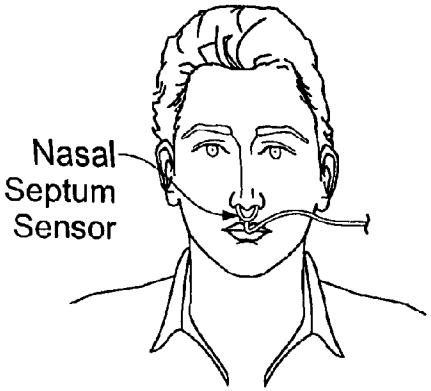
Figure 2D:
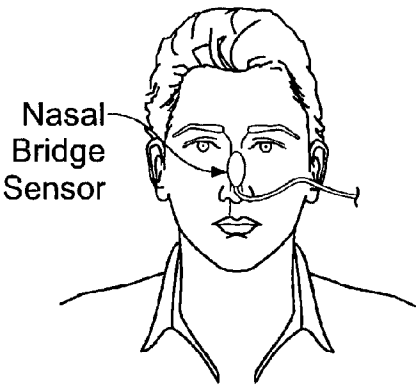
Figure 2E:
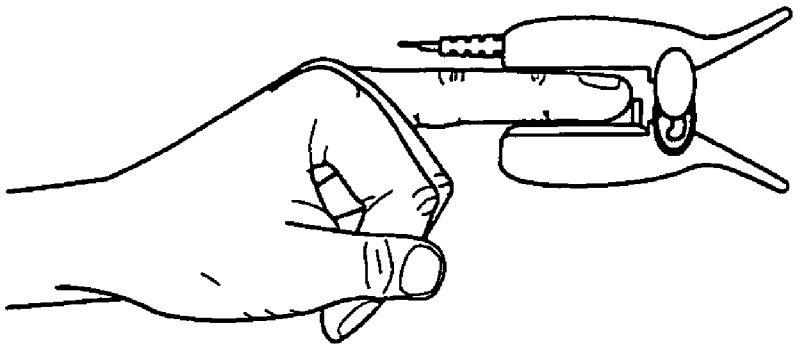
Figure 2F:
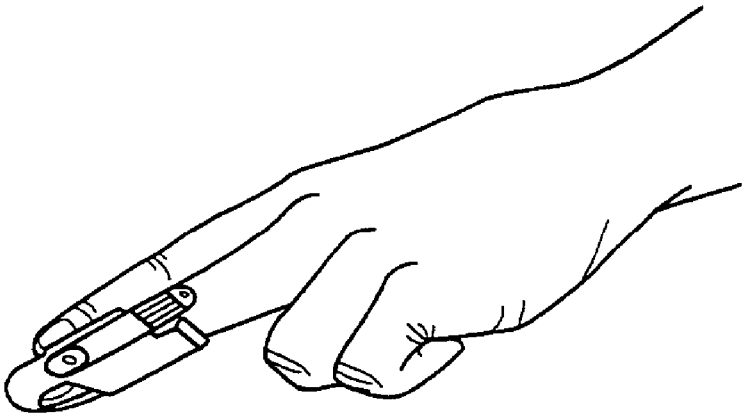

The descriptions below are more than sufficient for one skilled in the art to construct the disclosed implementations. Unless otherwise mentioned, the processes and manufacturing methods referred to are ones known by those working in the art FIG. 1 shows a defibrillator 10 connected to a patient 20. Cable 12 connects the defibrillator to an electrode assembly 14, which supports two chest electrodes 16, 18, an accelerometer 20 (for measuring chest compression), and a pulse sensor 22 (e.g., an optical plethysmographic sensor). All wiring for the electrodes, accelerometer, and pulse sensor are bundled together in cable 12.

Figure 10B:
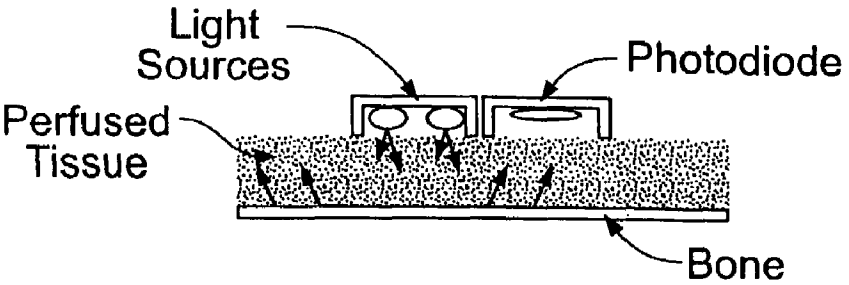
FIG. 10B is a diagrammatic view of a reflectance optical sensor.
Figure 10A:
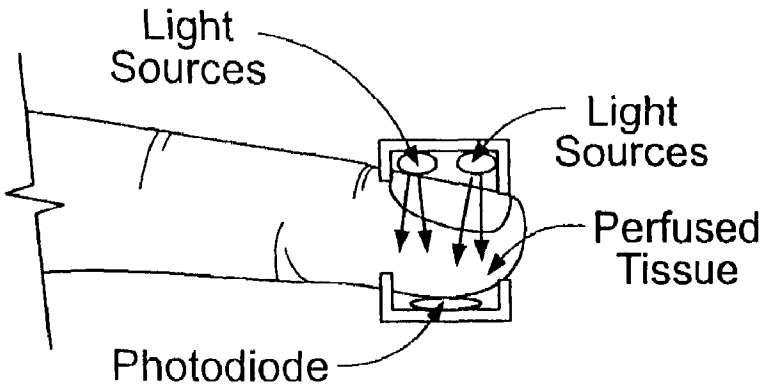
FIG. 10A is a diagrammatic view of a transmittance optical sensor.

FIGS. 2A-2F show alternative locations for the pulse sensor in the event the sensor is an optical plethysmographic sensor 22 (some of the same locations may be useful with other types of pulse sensors): anywhere on the forehead, the bridge of the nose, the septum of the nose, the ear lobe, the sternum above the accelerometer, and on any of the fingers or thumb. All of the sensors shown are commercially available, except the nasal septum and sternum sensor. The nasal septum sensor would be a transmittance sensor (e.g., as shown in FIG. 10A), similar to that available for the ear lobe. The sternum sensor would be a reflectance sensor (e.g., as shown in FIG. 10B).

The optical plethysmographic sensor 22 detects transmitted or reflected light, and provides a pulse signal 34, which represents a parameter correlated with the patient's pulse. In the case of an optical plethysmographic sensor, the pulse signal 34 would be an optical signal representing the brightness of light transmitted through or reflected from a portion of the body through which blood capillaries extend. The term "pulse signal" is simply a shorthand for an electrical signal representative of a parameter correlated with the pulse of the patient. E.g, in the case of an optical sensor, the pulse signal could be the light sensed by the optical receiver. If the patient has a pulse, there will generally be a pulsing variation in the pulse signal. In the case of an optical sensor, the variation will be in the absorption of light by the blood capillaries.

A variety of signal processing techniques may be used to process the pulse signal to determine whether a pulse is present or absent. Several possibilities are described below. These may be used alone or in combination.

One processing technique is to process the pulse signal 34 to isolate any pulsatile component. FIG. 3 shows a typical pulse signal 34 that would be detected when a pulse is present. A time domain analysis can be performed on the pulse signal to determine whether it contains a pulsatile component. For example, the non-pulsatile component can be estimated as the mean of the pulse signal, and variation from the mean can be analyzed for the presence of a pulsatile component indicative of a pulse. The frequency and strength of the pulsatile component (i.e., the variation from the mean) can be compared to predetermined frequency ranges and strength ranges to decide whether a pulse is present.

Figure 3A:
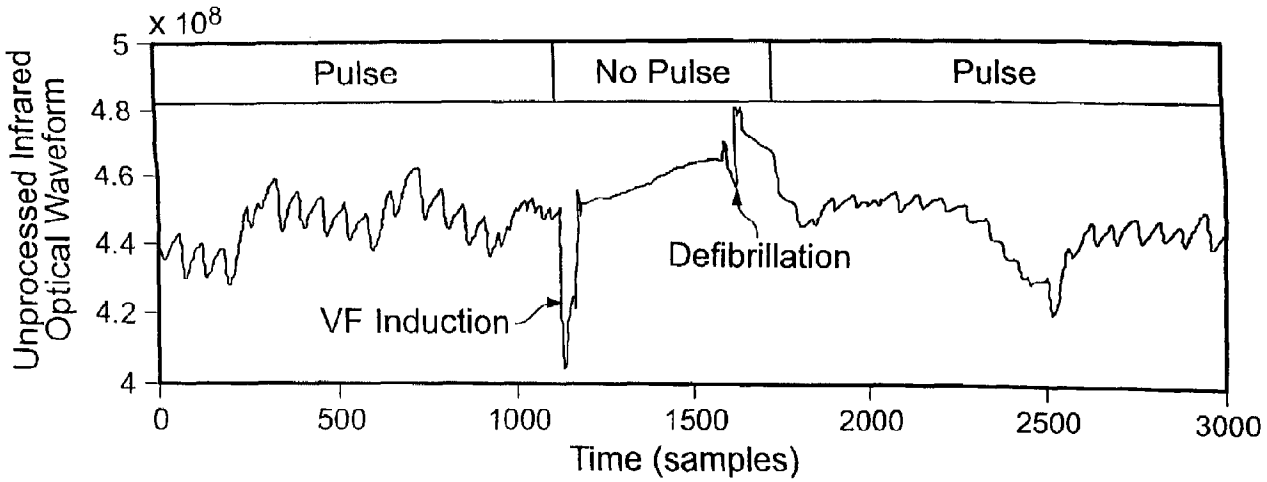
FIG. 3A shows an unprocessed pulse signal from a pulse sensor.

The pulse signal may be filtered so that pulses in the waveform are enhanced and then detected with a beat detection algorithm (e.g., the algorithm conventionally utilized for ECG R-wave detection). The filtering may include a high pass filter, a low pass filter, and also a notch filter to remove line noise if necessary. The high pass filter with a −3 dB cutoff frequency near 0.5 Hz removes any DC component, thus enhancing any existing pulsatile component. The low pass filter, with a −3 dB point in the range of 5-15 Hz removes some signal components unrelated to patients' pulse (i.e., noise). A smoothed or unsmoothed difference operation may also be applied to the pulse signal as one method to enhance or precondition the pulse signal for a time-domain beat detection algorithm. FIG. 3A illustrates a raw pulse signal, and FIG. 3B shows a filtered, preconditioned pulse signal ready to be processed by a beat detection algorithm.

Figure 3B:
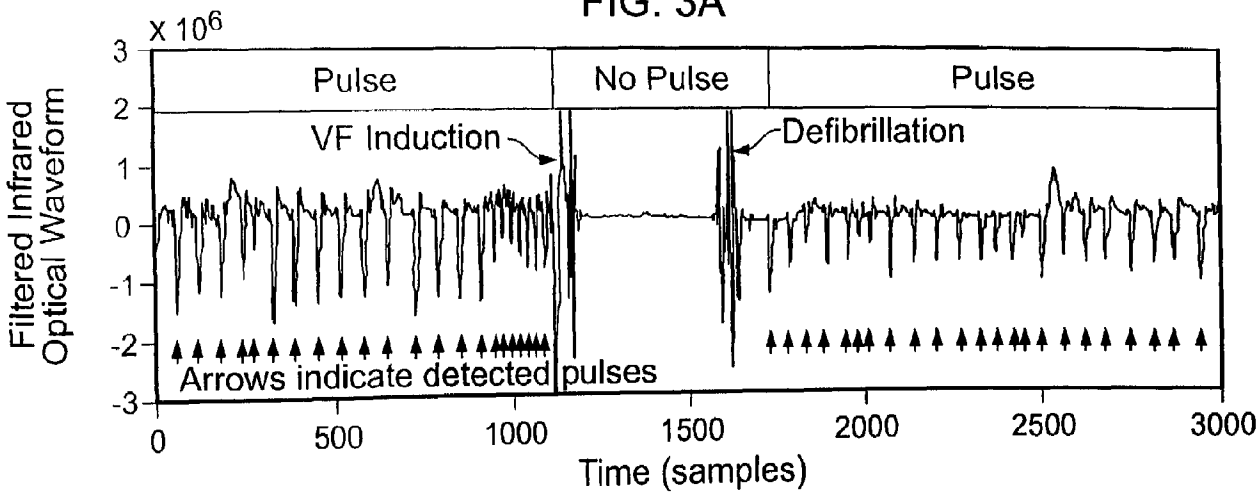
FIG. 3B shows a filtered pulse signal, preconditioned for beat detection.
Figure 4:
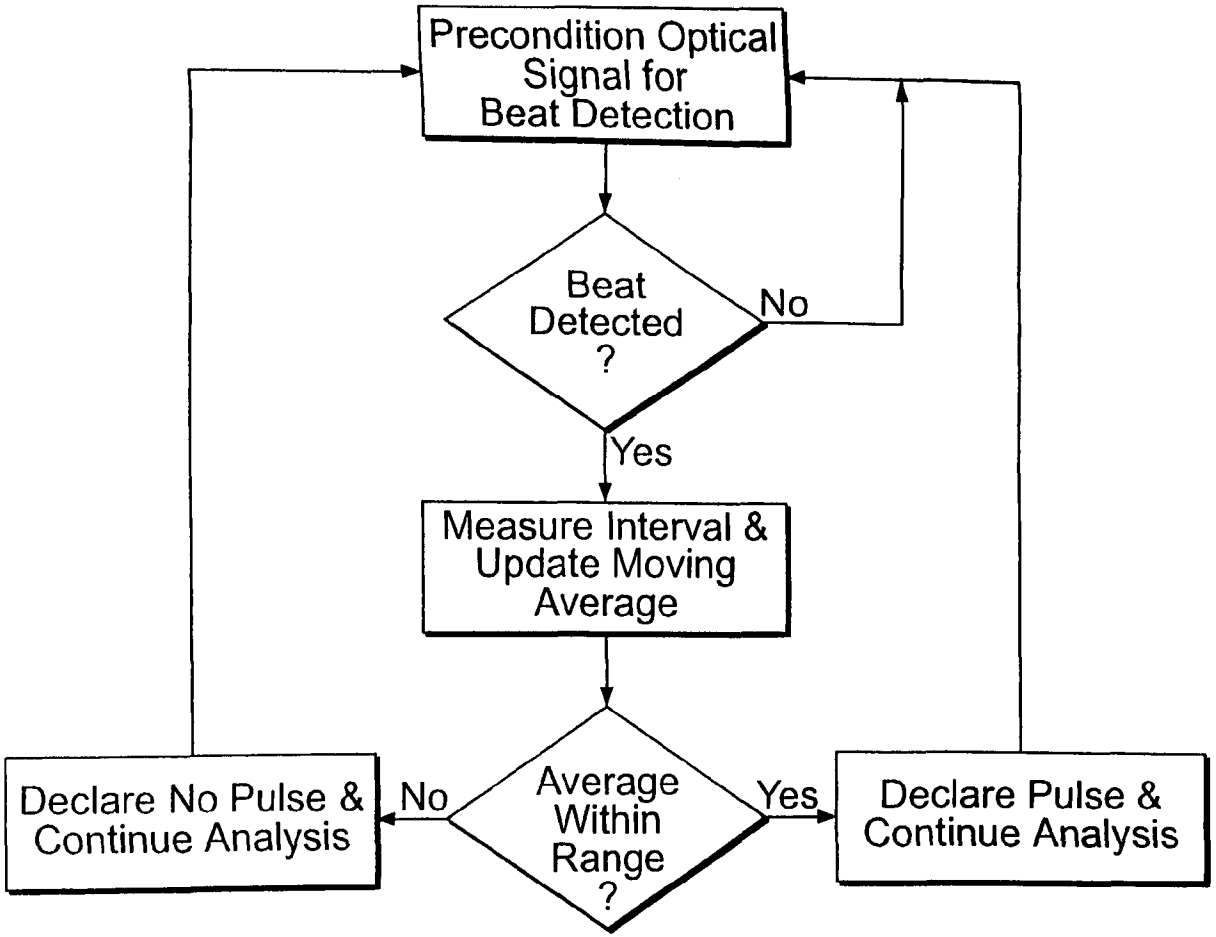
FIG. 4 is a block diagram of an algorithm used in one implementation of the invention.

The beat detection algorithm of FIG. 4 may be applied to the preconditioned pulse signal of FIG. 3B. The beat detection algorithm is intended to identify individual pulses within the pulse waveform. The arrows at the bottom of FIG. 3B indicate detection of a beat by the algorithm. Time intervals may then be computed between any two successive pulse detections. These time intervals, derived from the pulse waveform, may then by analyzed to determine the likelihood of a pulse. A moving average of these intervals may also be computed and updated as new intervals are measured. If the average interval is within a range (e.g. 35-185 beats/minute), then a pulse might be declared present.

Another processing technique is to use both a pulse signal from the pulse sensor and an ECG signal from the electrodes. Typically, both the pulse signal and the ECG signal will exhibit periodicity when a pulse is present, because a true pulse originates from a mechanically beating heart, and thus the same periodicity observed on the pulse signal should be present on the ECG signal when the heart is beating. However, a periodic ECG signal is not always indicative of a pulse, and thus should only be used to verify (or in combination with) periodicity detected in the pulse signal.

Figure 5:
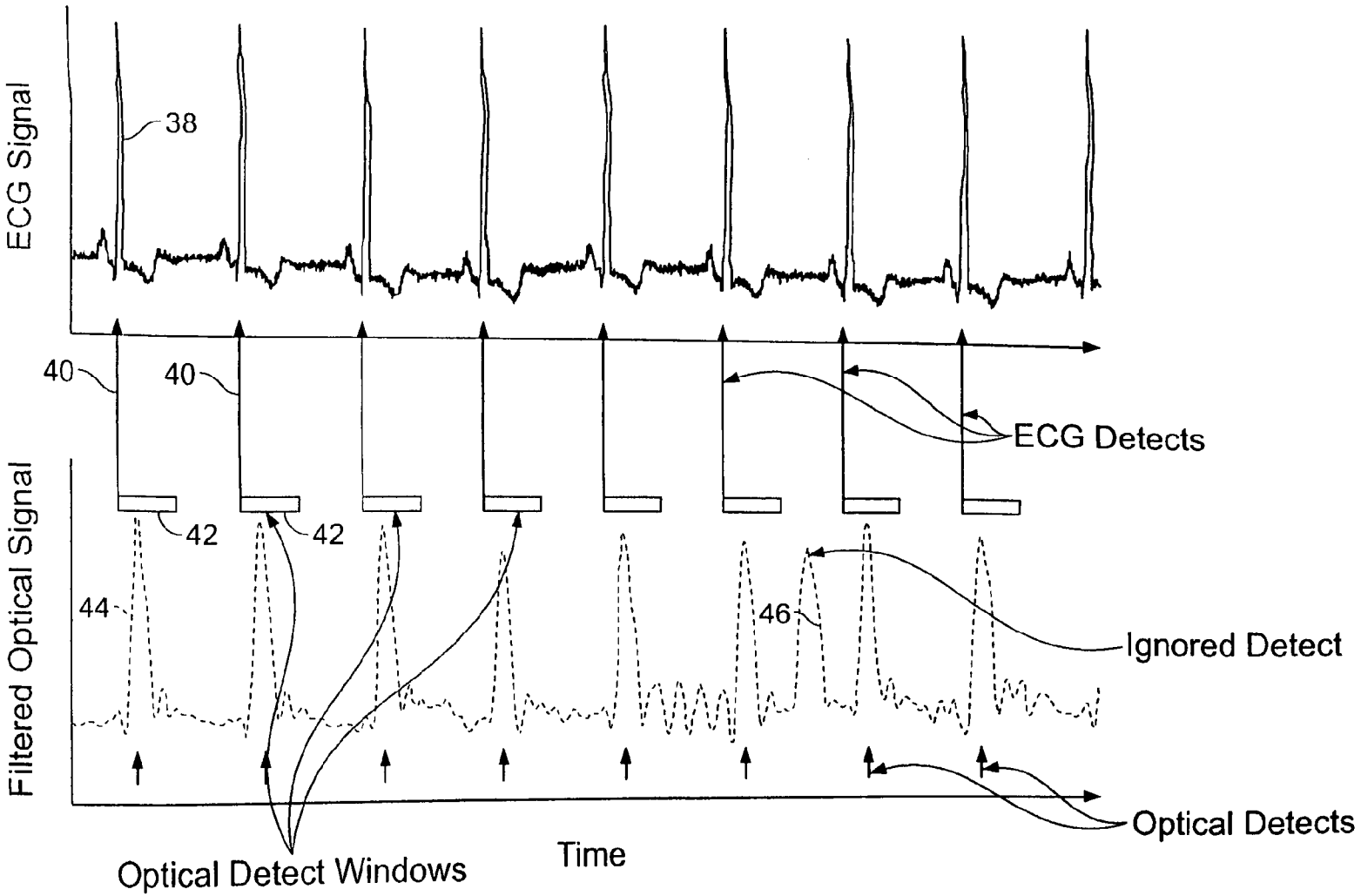
FIG. 5 illustrates how an ECG signal is used in conjunction with the pulse signal from the pulse sensor.
Figure 6:
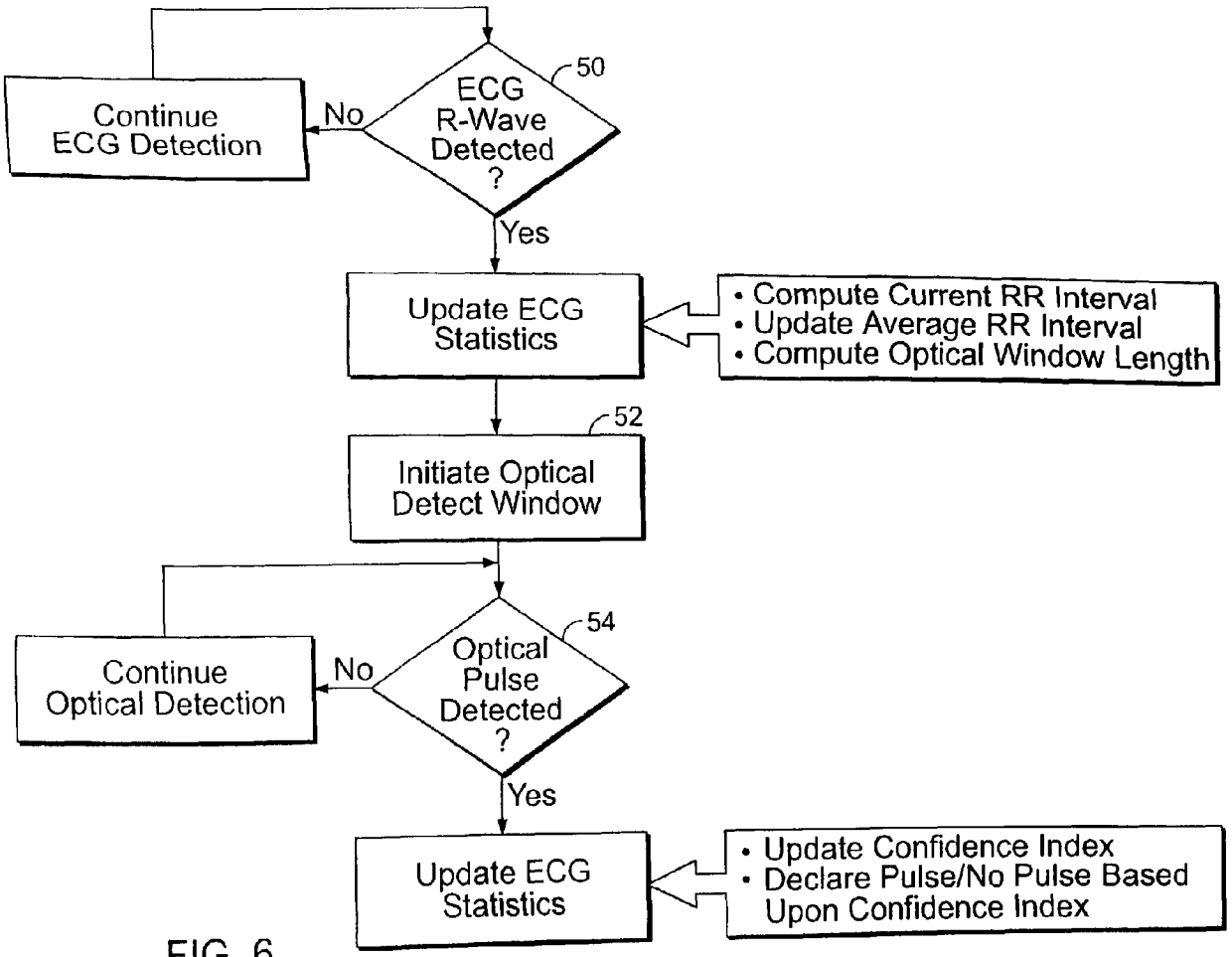
FIG. 6 is a block diagram of an algorithm for using an ECG signal in conjunction with the pulse signal.

FIG. 5 shows an ECG signal 38 in the upper half of the figure and the filtered, pulsatile component 44 of the pulse signal in the lower half of the figure. FIG. 6 shows the algorithm followed in processing the signals. Upon detecting (50 in FIG. 6) an ECG R-wave (ventricular depolarization) 40 a time window 42 is initiated (52 in FIG. 6). The duration of a time window may change as a function of the previous ECG cycle length or current average ECG cycle length. This variable window length is intended to shorten for shorter cycle lengths (high heart rates) and lengthen for longer cycle lengths (lower heart rates). During that time window, the pulsatile component 44 of the pulse signal is analyzed for a corresponding pulse (54 in FIG. 6). The pulse signal is not analyzed outside of this time window, thereby reducing the number of false detections on the pulse signal. Alternatively, the entire pulse signal is analyzed and pulse detects outside of an R-wave initiated time window are ignored. Detection of a pulse on the pulse signal within the time window could be sufficient to conclude that a pulse is present. Greater confidence that a pulse is present can be had using a confidence index that is increased each time a pulse is detected in the pulse signal during the prescribed time window following an R-wave. In FIG. 5, all of the pulse pulses, except the seventh pulse 46, are detected and considered as valid detects since they are within time windows initiated by R-wave detections on the ECG signal. The portion of the pulse waveform comprising the seventh pulse 46 is either not analyzed or detected and ignored since it is outside of an pulse detect time window. One possible confidence index would be the percentage of instances in which a pulse is detected in a window following detection of an R-wave. If the confidence index exceeds an empirically determined threshold, the existence of a pulse is declared. Otherwise a pulse is considered to be absent.

A simpler technique is to determine the pulse rate of each of the ECG and pulse signals, and simply compare the two pulse rates. If the difference between the two rates is within a range (e.g., 1-5 beats/minute), the existence of a pulse is declared. This technique may be used in conjunction with the pulse windowing scheme to minimize the number of false positive detections on the pulse signal. If the implementation does not employ a method (e.g., windowing scheme) to minimize false positive detections on the pulse signal, then the comparison between pulse and ECG derived pulse rates may be modified. In this case the absence of a pulse would be declared if the pulse rate is less than the ECG rate. This modification takes into consideration that the pulse rate may be higher than the ECG rate due to false pulse detections, and such a condition may be indicative of a pulse despite the difference between the two rates being outside of a range.

Another technique is to compare band-limited versions of the ECG and pulse signals. The signals can be band limited over a range of likely pulse frequencies (e.g., 0.5-5 Hz). The band-limited signals are compared to determine if a pulse or peak frequency of the pulse signal compares well with a pulse or peak frequency of the ECG signal. If the two compare well, the existence of a patient pulse is supported. Comparisons can be made using several different quantitative techniques. Cross correlation (convolution) of the two filtered waveforms is one technique that can be used to quantify the comparison of the two waveforms.

Figure 7:
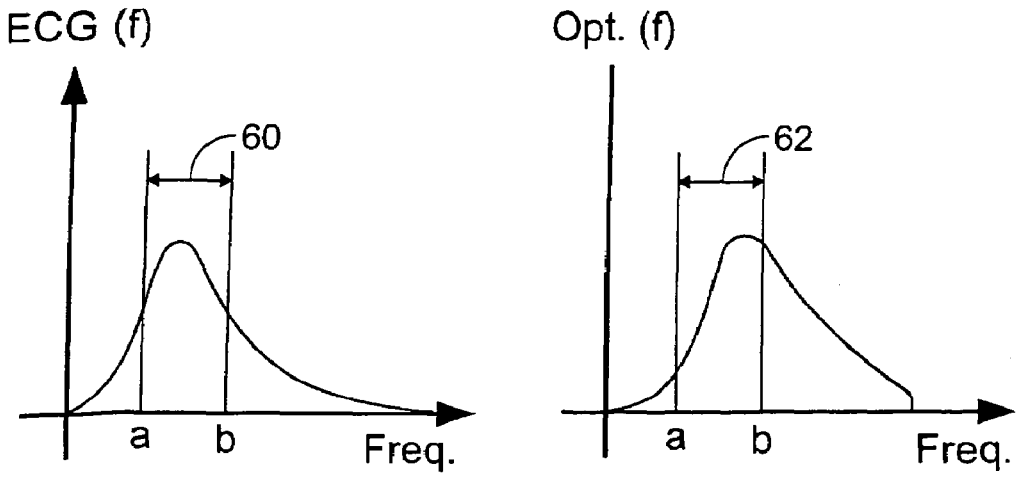
FIGS. 7 and 8 illustrate other implementations of the invention, in which the frequency transforms of the ECG and pulse signals are compared.

One technique for comparing the peak frequencies of the two signals is shown in FIG. 7. Each of the ECG and pulse signals is transformed into a frequency domain using, e.g., an FFT, wavelet, or other transform. The frequency peak of the transformed pulse signal is then compared with the ECG derived heart rate or peak frequency. An association between the two frequency peaks supports the existence of a pulse. A quantitative technique for determining how well the two frequency peaks compare is suggested in FIG. 7. The energy levels in discrete frequency bands are compared, e.g., the a-b band 60 in the ECG transform is compared to the a-b band 62 in the pulse signal transform.

Figure 8:
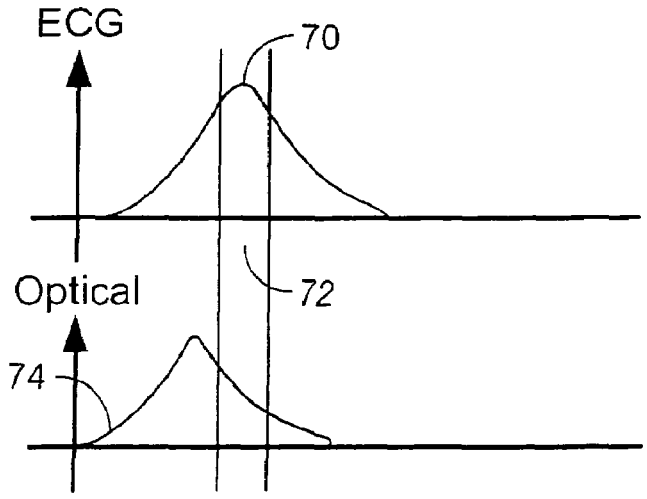

The peak frequencies can also be compared by examining one signal for a peak located within a predetermined frequency band centered on the peak frequency of the other signal. For example, as shown in FIG. 8, the peak ECG frequency 70 could be measured and updated at regular intervals (which could be constant or variable as a function of heart rate), with the measurement being done either in the time domain or in a transformed frequency domain. The pulse signal 74 would then be examined for a corresponding peak frequency within a band 72 centered on the continuously updated peak ECG frequency (e.g., using an adaptive filter). The existence of a peak on the pulse signal within the ECG determined band supports the existence of a pulse. In FIG. 8, the peak in the pulse signal is outside the band, thus suggesting that a pulse is not present.

The autocorrelation of the ECG signal can also be compared with the autocorrelation of the pulse signal. Comparing autocorrelation signals improves the signal to noise ratio and may be particularly useful if the periodic component of the signals is small. The two autocorrelation signals may be compared using a cross-coeerlation. The comparison determines if the periodicity of the two autocorrelated signals are similar. Similar periodicities support the existence of a pulse.

The addition of a pulse detection system adds significant improvements to automatic and semi-automatic external defibrillators. The addition of a pulse detection system will reduce the number of inappropriate shock advisements. Particularly in cases where patients have a pulse, but have been incorrectly classified by the ECG analysis algorithm as having a shockable rhythm. As shown in the table of FIG. 9, the addition of the pulse detection system will override the shock advisement from the ECG analysis algorithm thereby appropriately inhibiting defibrillation therapy. The addition of a pulse detection system will also enable the defibrillator to advise the rescuer when CPR is appropriate and inappropriate. In the case where the ECG analysis algorithm advises "No Shock" and the pulse detection algorithm indicates "No Pulse", the defibrillator may indicate to the rescuer that CPR should be administered. Conversely, detection of a pulse by the pulse detection system may be used to indicate to the rescuer that CPR is no longer necessary.

The pulse detection system may also be used to improve the defibrillator system by providing feedback to the rescuer during the administration of CPR. In this scenario, the pulse detection system may be utilized to monitor the effect that chest compressions have on a patients pulse. The detected magnitude and frequency of a pulse by the pulse detection system may be used independently or in conjunction with accelerometer data to aid the rescuer in delivering optimal CPR to the victim. Whereas an accelerometer may be used to measure the rate and depth of delivered chest compressions, a pulse detection system may be used to determine if these chest compressions actually result in the movement of blood thus resulting in a pulse.

A wide variety of pulse sensors may be used. For example, the sensor could be optical or non-optical. It could include an acoustic sensor (e.g., amplified stethoscope signals) for detecting heart sounds characteristic of a beating heart. It could include a sensor capable of mechanical or ultrasonic measurement (e.g., piezoelectric) of arterial wall motion—e.g., in locations such as the neck (carotid arteries), arms (radial and brachial arteries), and legs (femoral artery) where the arteries are relatively close to the surface. It could include an ultrasonic measurement of blood flow (e.g., such as the ultrasonic blood flow detectors used to detect carotid and/or femoral artery stenosis). It could include a pressure sensor that measures variation in the pressure in a limb-compressing pneumatic cuff. The sensor could employ impedance techniques for monitoring blood flow into and out of an arterial bed, e.g., as now used to non-invasively measure pulsatile cardiac output by measuring impedance across the chest. The same approach could be applied to other part of the body where pulsatile blood flow exists.

Both invasive (e.g., direct measurements of a parameter) and non-invasive (indirect measurements of a parameter) sensors can be used The examples given above are generally non-invasive. But invasive sensors could also be used, including, for example, pressure sensors coupled to a patient's vascular pressure via a liquid filled catheter, or intravascular pressure sensors, in which the sensor is incorporated onto the tip of a catheter placed in the vascular system.

Many other implementations of the invention other than those described above are within the invention, which is defined by the following claims.

What is claimed is:

[1. A cardiac resuscitation device, comprising a pulse sensor configured to detect pulse information characterizing the cardiac pulse in the patient, wherein the pulse sensor has a pulse sensor output signal as its output, and wherein the pulse sensor output signal contains information characterizing individual pulses, each corresponding to movement of blood in the patient's circulatory system;

an accelerometer configured to detect chest movements of the patient during a series of individual chest compressions, wherein the accelerometer has an accelerometer output signal as its output; and memory and processing circuits configured to process the pulse sensor output signal in conjunction with the accelerometer output signal to determine, for each of a plurality of individual chest compressions in the series of individual chest compressions, if the individual chest compression actually caused movement of blood thus resulting in an individual pulse.]

[2. The device of claim 1 wherein the device comprises a defibrillator for delivering a defibrillation waveform to the patient and chest electrodes for detecting at least one ECG signal on the patient and for delivering a defibrillation waveform to the patient.]

[3. The device of claim 2 wherein the memory and processing circuits are further configured to analyze the pulse sensor output signal in conjunction with the ECG signal.]

[4. The device of claim 3 wherein the pulse rate of the pulse signal is compared to the pulse rate of the ECG signal.]

[5. The subject matter of claim 2 wherein the defibrillator comprises an automatic external defibrillator (AED).]

[6. The subject matter of claim 5 further comprising the capability to provide the user with prompts for performing CPR, and wherein the prompts are dependent at least in part on whether the processing of the pulse signal determines that individual chest compressions actually cause movements of blood and thus individual pulses.]

[7. The device of claim 1 wherein the memory and processing circuits are configured to process the accelerometer output signal to determine the rate and depth of delivered individual chest compressions.]

[8. The device of claim 1 wherein the memory and processing circuits are configured to process the pulse sensor output signal to determine the magnitude and frequency of the patient's pulse.]

[9. The subject matter of claim 1 wherein the memory and processing circuits are further configured to determine the efficacy of CPR treatment of the patient.]

*10. A cardiac resuscitation device, comprising*

*a pulse sensor configured to detect pulse information characterizing the cardiac pulse in the patient, wherein the pulse sensor has a pulse sensor output signal as its output, and wherein the pulse sensor output signal contains information characterizing individual pulses, each corresponding to movement of blood in the patient's circulatory system;*

*a sensor configured to detect chest movements of the patient during a series of individual chest compressions, wherein the sensor has a sensor output signal as its output; and*

*memory and processing circuits configured to process the pulse sensor output signal in conjunction with the sensor output signal to determine, for each of a plurality of individual chest compressions in the series of individual chest compressions, if the individual chest compression actually caused movement of blood thus resulting in an individual pulse,*

*wherein the pulse sensor and memory and processing circuits are further configured to provide the user with prompts for performing CPR, and wherein the prompts*

*are dependent at least in part on whether the processing of the pulse signal determines that individual chest compressions actually cause movements of blood and thus individual pulses.*

*11. A cardiac resuscitation device, comprising*

*a pulse sensor configured to detect pulse information characterizing the cardiac pulse in the patient, wherein the pulse sensor has a pulse sensor output signal as its output, and wherein the pulse sensor output signal contains information characterizing individual pulses, each corresponding to movement of blood in the patient's circulatory system;*

*a sensor configured to detect chest movements of the patient during a series of individual chest compressions, wherein the sensor has a sensor output signal as its output; and*

*memory and processing circuits configured to process the pulse sensor output signal in conjunction with the sensor output signal to determine, for each of a plurality of individual chest compressions in the series of individual chest compressions, if the individual chest compression actually caused movement of blood thus resulting in an individual pulse,*

*wherein the pulse sensor and memory and processing circuits are configured to process the pulse sensor output signal throughout a cardiac resuscitation to determine when the patient exhibits a pulse sufficient to not require further CPR.*

*12. The device of claim 11 wherein the pulse sensor and memory and processing circuits are configured to provide the user with a prompt indicating that further CPR is not required.*

*13. A cardiac resuscitation device, comprising*

*a pulse sensor configured to detect pulse information characterizing the cardiac pulse in the patient, wherein the pulse sensor has a pulse sensor output signal as its output, and wherein the pulse sensor output signal contains information characterizing individual pulses, each corresponding to movement of blood in the patient's circulatory system;*

*a sensor configured to detect chest movements of the patient during a series of individual chest compressions, wherein the sensor has a sensor output signal as its output; and*

*memory and processing circuits configured to process the pulse sensor output signal in conjunction with the sensor output signal to determine, for each of a plurality of individual chest compressions in the series of individual chest compressions, if the individual chest compression actually caused movement of blood thus resulting in an individual pulse,*

*wherein the pulse sensor and memory and processing circuits are configured to process the pulse sensor output signal throughout a cardiac resuscitation to inform the user of when the patient's pulse returns.*

* * * * *